United States Patent [19]
Newman

[11] Patent Number: 5,831,146
[45] Date of Patent: Nov. 3, 1998

[54] GAS SENSOR WITH MULTIPLE EXPOSED ACTIVE ELEMENTS

[75] Inventor: Robert L. Newman, Osceola, Ind.

[73] Assignee: CTS Corporation, Elkhart, Ind.

[21] Appl. No.: 872,817

[22] Filed: Jun. 11, 1997

Related U.S. Application Data

[60] Provisional application No. 60/017,112 May 9, 1996.

[51] Int. Cl.⁶ .......................... G01N 25/32; G01N 27/18; G08B 17/10
[52] U.S. Cl. .................... 73/23.31; 73/25.03; 73/335.02; 73/23.2; 324/610
[58] Field of Search .............................. 73/23.31, 204.25, 73/23.2, 23.32, 25.01, 25.03, 335.02; 324/610

[56] References Cited

U.S. PATENT DOCUMENTS

| | | | |
|---|---|---|---|
| 3,221,320 | 11/1965 | Yoneda | 340/237 |
| 3,237,181 | 2/1966 | Palmer | 340/237 |
| 3,239,828 | 3/1966 | Peterman | 340/237 |
| 3,399,398 | 8/1968 | Becker et al. | 340/237 |
| 3,519,391 | 7/1970 | Winter et al. | 23/232 |
| 3,590,628 | 7/1971 | Orr | 73/23.1 |
| 3,606,790 | 9/1971 | Matsumoto et al. | 73/27 |
| 3,616,677 | 11/1971 | Oppegaard | 73/27 |
| 3,683,671 | 8/1972 | Van Swaay | 73/27 R |
| 3,961,248 | 6/1976 | Kawamura | 324/71 SN |
| 4,020,480 | 4/1977 | Gotley et al. | 340/237 R |
| 4,033,169 | 7/1977 | Fujishiro et al. | 73/23 |
| 4,039,852 | 8/1977 | Miyamoto et al. | 307/326 |
| 4,305,724 | 12/1981 | Micko | 23/232 E |
| 4,313,907 | 2/1982 | McNally | 422/97 |
| 4,332,772 | 6/1982 | McNally | 422/97 |
| 4,413,502 | 11/1983 | Ohta et al. | 73/23 |
| 4,476,096 | 10/1984 | Hoht | 422/96 |
| 4,696,188 | 9/1987 | Higashi | 73/204 |
| 4,793,181 | 12/1988 | Djorup | 73/336.5 |
| 4,816,800 | 3/1989 | Onaga et al. | 338/34 |
| 4,817,414 | 4/1989 | Hagen et al. | 73/25 |
| 4,818,977 | 4/1989 | Alexander | 340/633 |
| 4,872,340 | 10/1989 | de Yong | 73/338 |
| 5,017,340 | 5/1991 | Pribat et al. | 422/98 |
| 5,055,269 | 10/1991 | Palumbo et al. | 422/96 |
| 5,400,643 | 3/1995 | De Angelis et al. | 73/31.06 |

*Primary Examiner*—Hezron E. Williams
*Assistant Examiner*—J. David Wiggins
*Attorney, Agent, or Firm*—Michael W. Starkweather; Dan Tychonievich; Mark P. Bourgeois

[57] ABSTRACT

A combustible gas detector or sensor having catalytic coated resistance sensing elements that uses a wheatstone bridge to sense the presence and concentration of any combustible gases in a gas stream that chemically react with such catalytic coatings. Wherein there is a power supply node electrically coupling one end of a first and second bridge of the wheatstone bridge. There is a ground node electrically coupling the first and second bridge at another end. There is a first and second metered node located on the first and second bridge respectively. There is a first catalytic sensor element, located on the first bridge between the power node and first metered node. There is a second catalytic sensor element, located on the second bridge between the ground node and second metered node. There is a first reference sensor element, located on the first bridge and in series with the first catalytic sensor element, and coupled between the first metered node and the ground node. Finally, there is a second reference sensor element, located on the second bridge and in series with the second catalytic sensor element, and coupled between the second metered node and the power node the geometry and design of the gas detector has the two catalytic sensing elements and two reference sensing elements being spatially separated and positioned on a base capable of being rotated along an axis so that as the base rotates about the axis the heated gas stream will not contact the first and second reference sensing elements.

27 Claims, 7 Drawing Sheets

GAS SENSOR WITH MULTIPLE EXPOSED ACTIVE ELEMENTS

BACKGROUND OF THE INVENTION

Co-pending Patent Applications

This application is related to the following:

1) co-pending U.S. application Ser. No. 08/873,219, entitled A GAS SENSOR WITH ORIENTATION INSENSITIVITY, attorney docket no. CTS-1509, filed Jun. 11, 1997, 2) co-pending U.S. application Ser. No. 08/872,987, entitled A GAS SENSOR WITH MULTI-LEVEL INSENSITIVITY CIRCUITRY, attorney docket no. CTS-1518, filed Jun. 11, 1997, and 3) copending U.S. application Ser. No. 60/017,112, entitled, FUEL SYSTEM LOW CURRENT RHEOSTAT, attorney docket no. CTS-1491, filed May 9,1996.

The aforementioned are assigned to the assignee named in the present application and are herein incorporated by reference in their entirety.

1. Field of the Invention

This invention relates to the field of combustible gas detectors or sensors having both reference sensor elements and catalitic sensor elements exposed to the combustible hot gas stream without the use of a separate heating circuit.

2. Description of the Related Art

Various devices are well known for combustible gas detectors used to detect the presence of combustible gases such as those found in car engines. Typical circuits are configured to include at least one sensing element that may be a wire having a catalytic coating. The sensing element was used as one of four legs of a wheatstone bridge circuit. The other three legs consisted of two resistors and a compensator element. The compensator element was identical to the sensing element except that it did not bear a catalytic coating.

A current or voltage was applied to the bridge circuit to heat the surface of the catalytic coating affixed to the sensing element. Since the resistance values of the other three legs of the bridge were known, the resistance in the sensing element could be determined as the current or voltage was passed through the bridge.

When the sensing element was exposed to a combustible gas, such as hydrocarbon, the catalytic coating would begin to burn, increasing the temperature of the sensing element. As the temperature of the sensing element increased, the resistance of the element increased. Accordingly, the current passing through the element decreased. By comparing the resistance level of the sensing element to the resistance level of the compensator element, the presence of a combustible gas could be detected. Since the amount of gas caused a nearly linear increase or decrease in the resistance of the sensing element, the quantity of the gas could be accurately determined by calibrating the change in resistance. This is the basic operational principle of a catalytic combustible gas sensor.

3. Related Art

Examples of patents related to the present invention are as follows, and each patent is herein incorporated by reference for the supporting teachings:

U.S. Pat. No. 5,055,269, is a temperature limited catalytic gas detector apparatus.

U.S. Pat. No. 4,818,977, is a combustible gas detector having temperature stabilization capability.

U.S. Pat. No. 4,476,096, is a circuit arrangement for an apparatus for measuring and indicating the concentration of combustible gases and vapors contained in air.

U.S. Pat. No. 4,332,772, is a portable gas detector.

U.S. Pat. No. 4,313,907, is an apparatus for the detection of a combustible gas.

U.S. Pat. No. 4,039,852, is an exhalation inspecting apparatus.

U.S. Pat. No. 4,033,169, is a hydrocarbon concentration sensor for use in engine exhaust gas.

U.S. Pat. No. 4,020,480, is a catalytic detecting apparatus for detecting combustible gases and vapors.

U.S. Pat. No. 3,961,248, is a gas detector using gas sensing elements exhibiting different response characteristics.

U.S. Pat. No. 3,519,391, is a method of and apparatus for measuring combustible constituents of gas samples.

U.S. Pat. No. 3,237,181, is a gas detecting circuit.

U.S. Pat. No. 3,221,320, is a gas alarm circuit.

The foregoing patents reflect the state of the art of which the applicant is aware and are tendered with the view toward discharging applicants' acknowledged duty of candor in disclosing information that may be pertinent in the examination of this application. It is respectfully stipulated, however, that none of these patents teach or render obvious, singly or when considered in combination, applicant's claimed invention.

4. Related Problem

Figure 1:
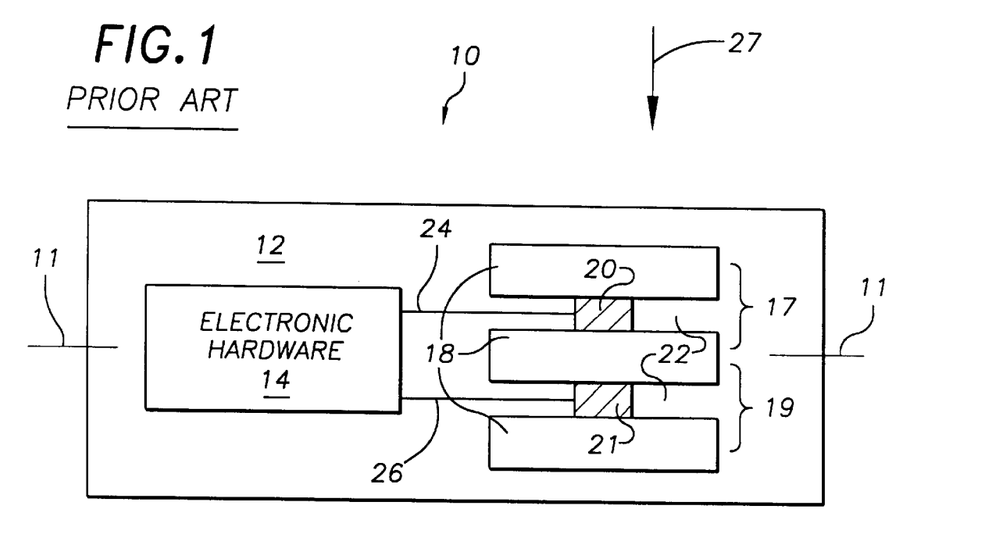
FIG. 1 is one embodiment of an undisclosed gas sensor designed by the inventors that illustrates one problem overcome by the preferred embodiments.

Referring to FIG. 1, there is a previous undisclosed design from the present inventors that illustrates one problem to be overcome by the additionally now disclosed preferred embodiments. Specifically, there is a sensor 10 having a base 12 with signal conditioning circuitry 14 that receives signals via traces 24 and 26 from sensing element structures 17 and 19, which are located on either side of longitudinal axis 11. Uniquely, the sensing element structures 17 and 19 are made up of sensing elements 20 and 21 that are located on parallel bridges 22 and thermally isolated by voids 18. In operation, one skilled in the art will realize that all of the electrical signals will be skewed if the heated air flow 27 first interacts with the catalyzed sensing element and then contacts the reference sensor. The air contacting the reference sensor will have been heated by the catalytic reaction, thus skewing any resulting signals. To avoid this problem, great care must be given to ensure that the air 27 does not contact the sensor elements in this fashion. In particular, the sensor would have to be placed so the air either hits both sensors simultaneously or hits the reference sensor first. In either case it is very difficult to make sure that the sensor is so arranged when placing it in an exhaust gas air stream. However, the present invention has overcome the need for careful placement of the sensor 10 in air stream 27 and thus eliminating the potential signal skewing problem.

This and other problems will be solved by the preferred embodiments of the invention. A review of the specification, drawings, and claims will more clearly teach a skilled artisan of other problems that are solved by the preferred embodiments.

SUMMARY OF THE INVENTION

It is a feature of the invention to provide a combustible gas detector or sensors having both reference sensor elements and catalytic sensor elements exposed to the combustible hot gas stream without the use of a separate heating circuit.

A further feature of the invention is to provide a gas detector that uses a wheatstone bridge. Wherein, there is a power supply node electrically coupling one end of a first and second bridge of the wheatstone bridge. There is a ground node electrically coupling the first and second bridge at another end. There is a first and second metered node located on the first and second bridge respectively. There is a first catalytic sensor element, located on the first bridge between the power node and first metered node. There is a second catalytic sensor element, located on the second bridge between the ground node and second metered node. There is a first reference sensor element, located on the first bridge and in series with the first catalytic sensor element, and coupled between the first metered node and the ground node. Finally, there is a second reference sensor element, located on the second bridge and in series with the second catalytic sensor element, and coupled between the second metered node and the power node.

A further feature of the invention is that the gas detector further comprises a base having one end for being heated by an element during operation of the gas detector, the wheatstone bridge located on the one end thereof.

A further feature of the invention is that during operation of the gas detector, a heated gas steam portion is created as the gas stream passes over the first and second catalyzed sensor element, the first and second catalyzed sensor elements and the first and second sensor elements are positioned on the base so that as the base rotates about the axis, the heated gas stream portion will not contact the first or second sensor element.

A further feature of the invention is that the base includes a catalyzed sensor section for mounting both the first and second catalyzed sensor elements on opposing sides thereof. Additionally, the base includes a sensor section for mounting both the first and second sensor elements on opposing sides thereof.

A further feature of the invention is that the catalyzed sensor section and the sensor section have a void on at least two sides thereof.

The invention resides not in any one of these features per se, but rather in the particular combination of all of them herein disclosed and claimed. Those skilled in the art will appreciate that the conception, upon which this disclosure is based, may readily be used as a basis for the designing of other structures, methods and systems for carrying out the several purposes of the present invention. Further, the abstract is neither intended to define the invention of the application, which is measured by the claims, neither is it intended to be limiting as to the scope of the invention in any way.

It is noted that the drawings of the invention are not to scale. The drawings are merely schematic representations, not intended to portray specific parameters of the invention. The drawings are intended to depict only typical embodiments of the invention, and therefore should not be considered as limiting the scope of the invention. In the drawings like numbering represents like elements between the drawings. In the drawings, like numbering represents like elements between the drawings.

DETAILED DESCRIPTION OF THE PREFERRED EMBODIMENT

Figure 2:
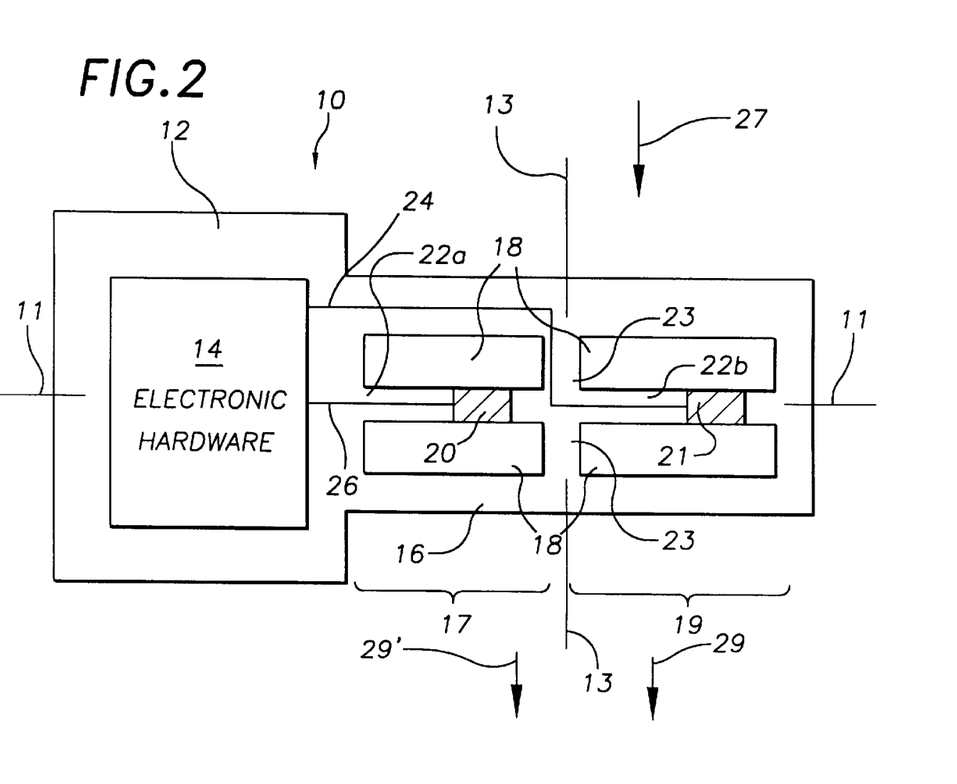
FIG. 2 is one embodiment of the invention.

The present invention provides a gas sensor for determining gas concentrations in an air stream. Referring to FIG. 2, there is a preferred embodiment of the gas sensor 10. Specifically, the gas sensor 10 has a base 12, which has a longitudinal axis 11 oriented to be at an angle to the gas stream 27, illustrated as generally perpendicular. There is also a reference sensor element 20 on base 12, and a catalyzed sensor element 21 proximate the reference sensor element 20. As known in the art, the catalyzed sensor element 21 creates an exothermic reaction upon contacting the gas stream thereby forming a heated gas stream portion 29. The gas stream flowing past the sensor element 20 would not create a heated gas stream portion 29'. The base also has an extension portion 16, located between the signal conditioning circuitry 14 and the sensor regions 17, 19, for creating a distance between the circuitry 14 and the heated sensor regions 17, 19. Although extension portion 16 is illustrated as relatively short, in reality it could be relatively long to protect the circuitry 14 from the detrimental high temperatures associated with the operational temperature ranges of the sensor elements 20, 21. The sensor regions 17, 19 could be operating, for example, from 200 to 500 plus degrees Celsius for proper operation. However, the conditioning circuitry 14 would need to be operated around a maximum of 150 degrees Celsius for optimum signal processing. Thus, by regulating the length of extension section 16, it is possible to keep the signal conditioning circuitry 14 in a proper operational temperature range.

In the present embodiment, both sensor elements 20, 21 are located upon two separate bridge sections 22a, 22b. Additionally, these bridge sections are isolated from any heat sink effects from the base 12 by voids 18 located on at least either side of the bridges. In this arrangement, it is possible to have both sensor elements 20, 21 closer in temperature so that any change in electrical resistance would not be due to ambient gas stream heat. Thus, only exothermic heat from the catalytic reaction on the measuring sensor element will cause a notable difference between the two resistances of the two sensor elements. It is advantageous to have both sensor elements to be close in temperature to avoid having compensating circuitry and other means for adjusting for the temperature differences. With various designs of the bridges, voids, and sensor elements, it is possible to have temperature differences below 80 degrees Celsius and optimumly below 50 degrees Celsius when operating in 200 to 600 degrees Celsius or more. It is noted that the ideal situation would be to have no difference in temperature between the sensor elements except for the exothermic catalytic reaction effects.

Of particular note, horizontal axis 13 separates sensor regions 17 and 19. It is this separation that provides for the advantage of orientation insensitivity. Specifically, the sensor 10 may rotate about axis 11 and in no position will the heated gas stream portion 29 affect the reference non-catalyzed sensor 20. This is a great advantage over the previous design considered by the inventors in FIG. 1, where the sensor is very orientation sensitive for proper operation. Of course, this situation only works if the gas stream is substantially perpendicular to the longitudinal axis 11. Also keep in mind that the gas stream most likely will already be heated but a skilled artisan will realize that the catalytic reaction with the gas will further heat the gas stream, thus creating the "extra" or catalyticly heated gas stream portion 29.

Figure 3:
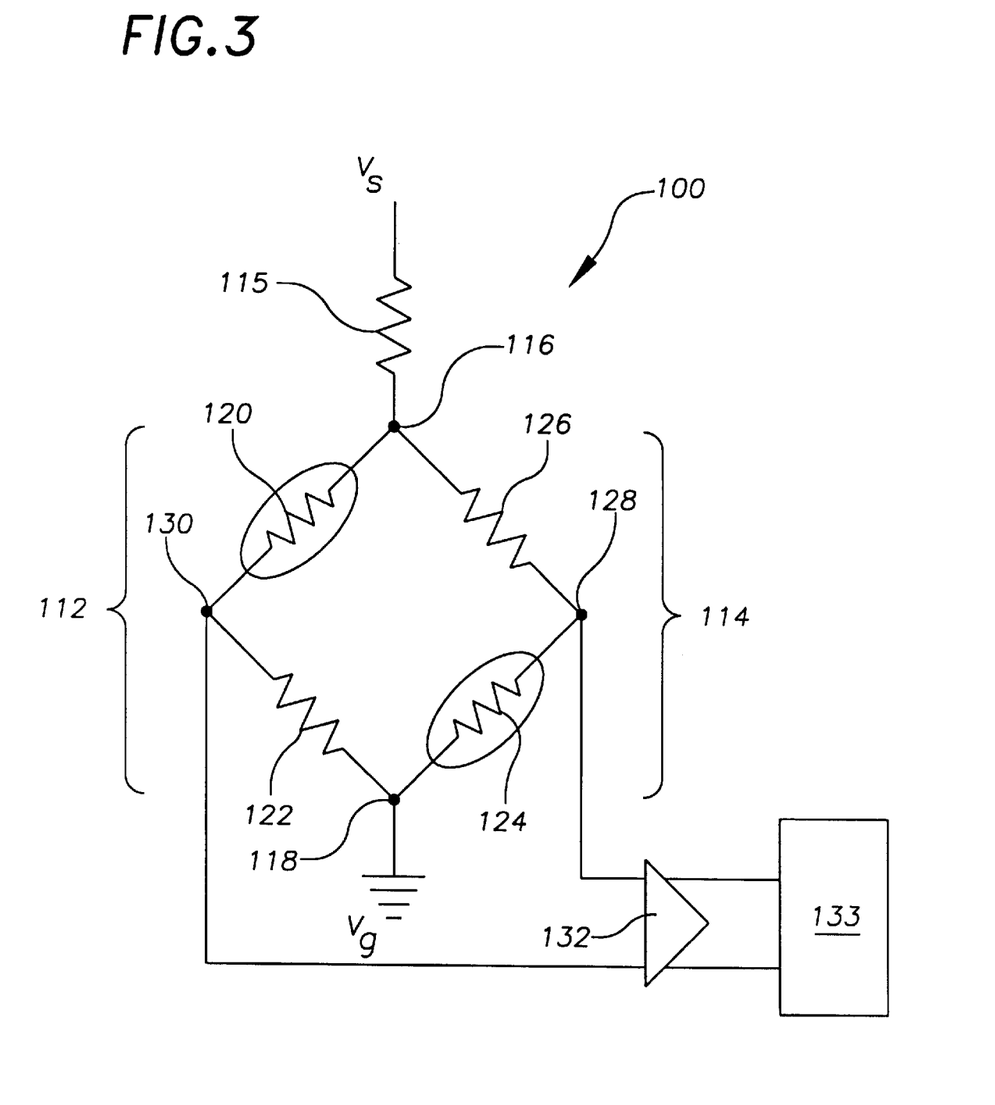
FIG. 3 illustrates a preferred wheatstone bridge circuit embodiment of the invention.

Referring to FIG. 3, there is illustrated a preferred wheatstone bridge embodiment. Specifically, there is a wheatstone bridge 100 having a first and second bridge 112, 114, a voltage source Vs coupled to a balancing resistor 115, a voltage source node 116 that couples one end of the two bridges 112,114, and a ground Vg coupled to a ground node 118 that couples the other end of the two bridges 112, 114. On each bridge are two sensor elements, a reference sensor element 122, 126, and a catalyzed sensor element 120, 124. Coupled between the two sensor elements are metered nodes 128, 130. Coupled to the metered nodes is an amplifier 132, and a voltage meter 133 coupled to the amplifier for first amplifying the analog signal and then converting the analog to a digital signal coupled to the other signal conditioning circuitry 14. The two catalyzed sensor elements 120, 124 are located on opposite sides of the base 12 but on the same bridge 22b, for example. The reference sensor elements 122, 126 are similarly arranged on opposite sides of the same bridge, for example bridge 22a. Thus, all four sensor elements will be located on the end of the sensor 10 that will receive direct impact from the gas stream 27. Of course, although the specification discusses the use of sensor elements, one skilled in the art realizes that each sensor 120, 122, 124, and 126, is a resistor.

One skilled in the art of designing sensor circuitry will understand that the circuit 100 will create a doubling of the output that can be read by the voltage meter 133 over prior art single sensor element wheatstone bridge circuits. In operation, there are two basic conditions—inactive and active. When circuit 100 is inactive or in a starting condition, all four resistors are set to be equally charged to achieve a balanced grid. Thus, when current is applied to each bridge 112,114, the voltage at nodes 130 and 128 are equal.

When circuit 100 is active or when a gas stream is applied to circuit 100, there is an increase in the temperature on resistor 120 and 124, but no change to 122 and 126. As discussed previously, as the temperature increases, the resistance increases. Thus, the resistances on resistors 120 and 124 are greater than resistances on resistors 122 and 126. In an ideal setting, the resistance resistor 120 equals resistor 124, just as the resistance on resistor 126 equals resistor 122. Because of the increased resistances, the voltage at node 130 is less than it was before the gas was applied. However, the voltage on node 128 is greater than it was before the gas was applied, because the resistance on resistor 124 is greater than resistor 126. In the ideal setting both nodes change the same amount but in opposite directions.

It is noted that in the prior art there is only one reference and one catalyzed sensor element and the other two resistors are fixed. It did not matter if the fixed resistors were in the bottom or the top or either side of the bridges, there would still be a shift in voltage, but it would only be one half the shift achieved by the preferred embodiment.

It is noted that the prior art has two of the wheatstone bridge resistors fixed. In other words, the fixed resistors are away from the gas and even in another chamber or on the circuit board, outside the heated environment. Thus, the prior art needs very precise temperature compensating circuitry to balance the bridges.

In the current preferred embodiment, no temperature compensating circuitry need be added to the sensor 10. By having all four resistors 120, 122, 124, and 126 in the heated gas stream, control of the temperature on all four resistors is achieved as a group. Temperature controlling circuitry is used, but the resistors on the wheatstone bridge circuit are used to create the heat by controlling the amount of current that flows therethrough. In the present design, the temperature of the sensor element doesn't have to be as accurately controlled as the prior art designs. The current invention does set a temperature, it is important to have elevated temperatures, but it is not needed to have the temperature exactly controlled, like 400 or 401 degrees Celsius. It is allowable to have, for example 400 , 410 or 420 degrees Celsius and still have accurate readings, because all of the resistors are dimensionally and chemically equal. With the prior art, to have a balanced bridge, it is mandatory to maintain accurate control of the temperature of the two non-fixed resistors—the catalyzed and reference resistors. Thus, the prior art uses heaters in the designs.

The preferred embodiment will operate over a temperature range from as low as the light off temperature of the gas to be sensed to as high as whatever temperature that would breakdown the resistance of the resistors in the wheatstone bridge. The light off temperature is that temperature needed for a gas to interact with the catalyst to create an exothermic reaction.

In operation, the preferred embodiment does use a set temperature for the sensor to operate at high temperatures. In particular, it is best to operate at temperatures hotter than the ambient temperature. The hotter than ambient controlled temperature provides a stable output. One skilled in the art will realize that resistors have the resistance change linearly as a function of increasing temperature. However, for elevated temperatures, there is a little curve to the linear function. The difference in resistance that you get for a given temperature change, gets less and less as you increase hotter and hotter. Therefore, a fixed temperature is chosen higher than expected ambient because to follow a changing high ambient temperature would lead to a gradually decreased output signal as the temperature got hotter and hotter. Thus, a predictable output signal is achieved by setting the temperature of the sensor elements to a consistent output of volts per part per million.

To achieve the relatively fixed elevated temperature, the preferred embodiment has regulated current running through the wheatstone bridge 100 to keep it at that selected temperature. Specifically, the resistors, which act as a heater when current goes through them, are turned on and off a proportional amount of time. A skilled artisan would know how to regulate the temperature by taking a voltage reading of nodes 116, and 118 and setting the total resistance of the wheatstone bridge by comparing it to the in-series resistor 115.

One of the advantages of the preferred embodiment is that the selected temperature can be changed without changing any of the hardware, ie. resistors. Thus, by simply changing the timing programming of the heating current, most any temperature can be used for the same sensor and wheatstone bridge unlike the prior art that would require a changing of the physical resistors. A key to allowing this flexibility not previously found is that the present preferred embodiment uses the same material for each resistor, all resistors are heated the same way (in the heated gas stream 27), and trimmed to be dimensionally all the same.

Figure 4:
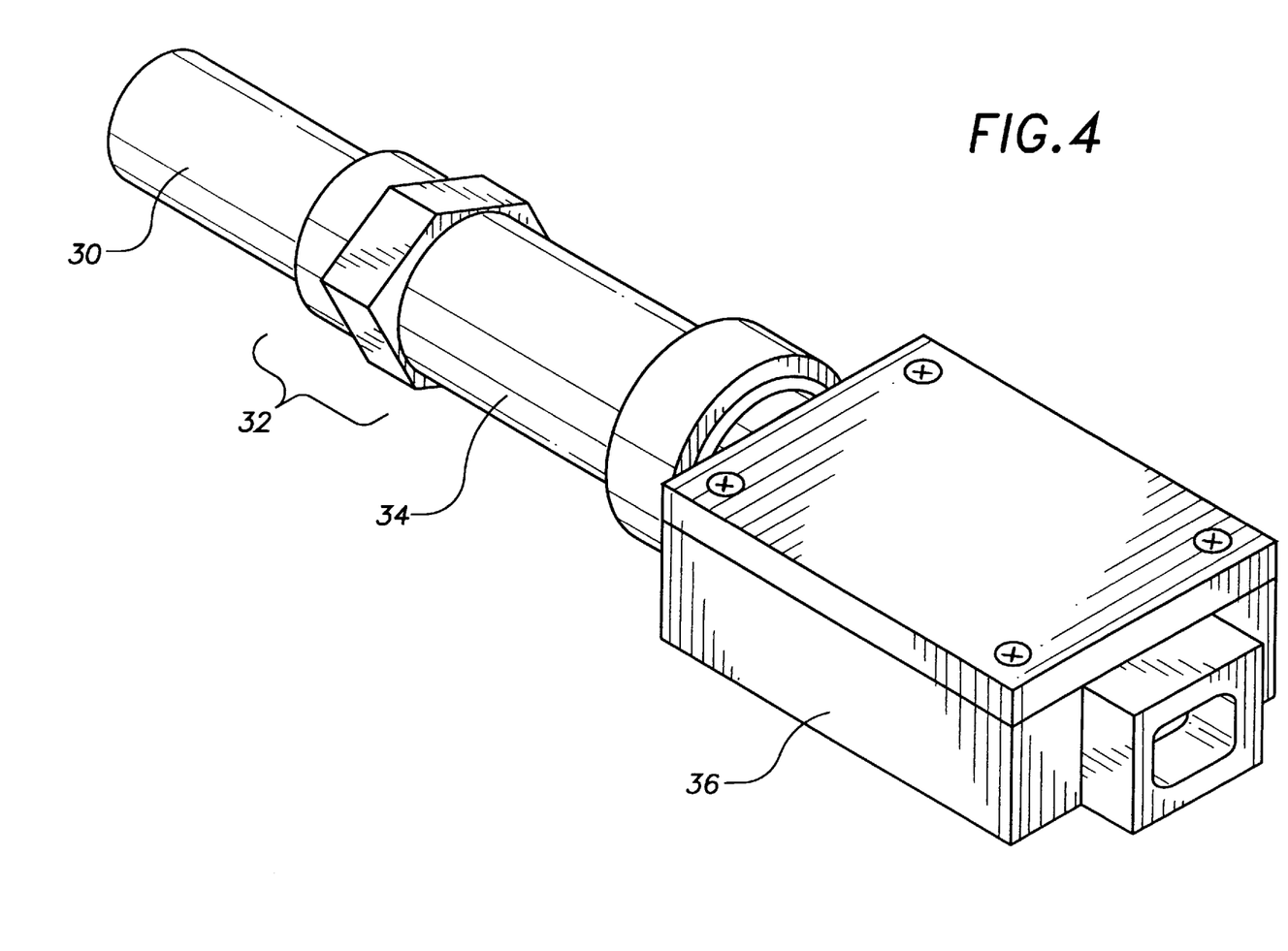
FIG. 4 illustrates a housing for holding the sensor.

Referring to FIG. 4, there is illustrated a housing for holding the sensor 10. In particular there is a hollow air pervious porous cap 30 for encapsulating the sensing elements 20, 21. There is also an attachment 32 for coupling the cap 30 to a spacer 34. The spacer serves the purpose of extending the electronics housing 36 far enough away from the cap 30, since the cap region is the hottest area and the housing holds the conditioning circuitry 14, which requires lower temperatures for proper operation. The electronics housing 36 protects the conditioning circuitry 14 and provides support for coupling the sensor to output wires to communicate with remote analysis circuitry (not shown). The whole assembly is mounted onto an exhaust pipe just after a catalytic converter. Of course only the porous cap 30 should be located in the exhaust pipe to remove the electronics from the hot temperatures.

The present invention provides a gas sensor having a multilayered structure. The structure is ideally suited to sensing hydrocarbons and nitrogen oxides in an automobile exhaust system. Regarding FIG. 5, there is a plan view of the gas sensor 10 showing part of a substrate (base) 12. Substrate 12 is preferably made out of a ceramic material but other suitable dielectric materials may be used. Only the portion of substrate 12 containing a catalytic support structure 50 and glass adhesion layer 46 has been included in FIG. 5.

Figure 5:
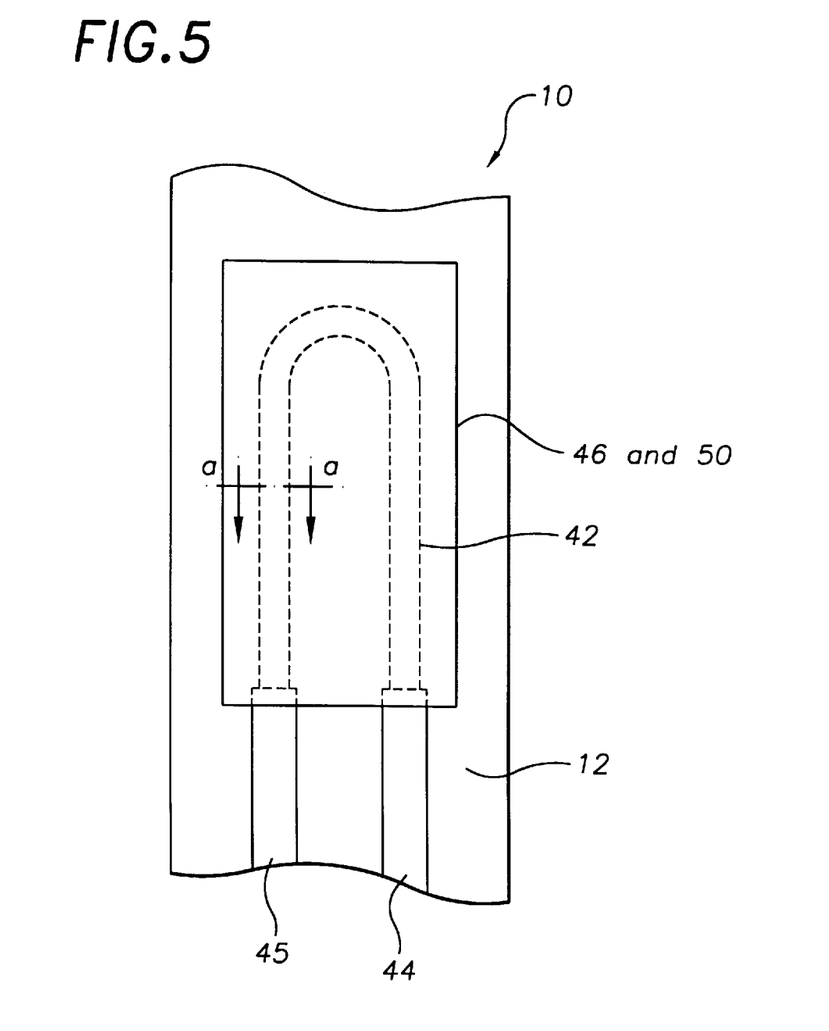
FIG. 5 is a plan view showing a closeup of the sensor element region.

The remaining portion of substrate 12 can take on any desired shape that will supply the necessary structural and thermal properties for the sensor. For instance, the structure must be strong enough to survive the shock and vibration attendant in an automobile exhaust system. In addition, the thermal properties must be such that any catalytic reactions occurring on catalytic support structure 50 can be detected by a thermally sensitive resistor element 42 located on substrate 12 (i.e. the substrate must not extract so much heat from the catalytic reaction that there is no resulting temperature increase in resistor element 42).

Located on substrate 12 and electrically connected to resistor element 42, are conductors 44 and 45. Conductors' 44 and 45 are connected to circuitry (not shown) that can detect resistance changes from accompanying voltage drops along the length of resistor element 42.

Figure 6:
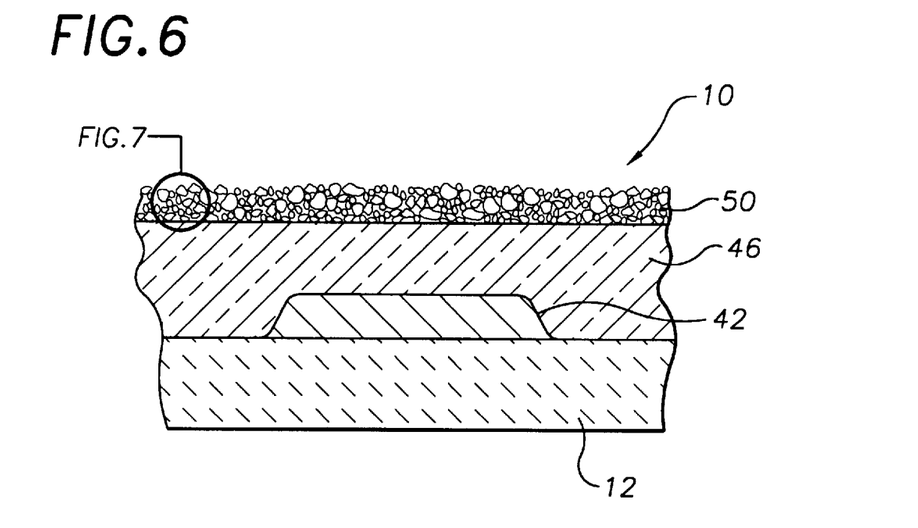
FIG. 6 is a cross-section of FIG. 5 taken through section a-a showing one embodiment for a multilayered structure.

In FIG. 6, a cross section taken through resistor element 42 is depicted. Resistor element 42 can be deposited on substrate 12 using any conventional thick or thin film technique since the deposit is robust enough to withstand the environment of an auto exhaust system and the thermal coefficient of resistivity is high enough so that the resistor will respond to temperature changes from catalytic reactions. The material used to form resistor element 42 can be selected using these same criteria. In the preferred embodiment, it was found that platinum is a suitable material for resistor element 42 and that screen printing proved to be a suitable deposition method.

Conductors 44 and 45 can also be deposited using any conventional thick or thin film technique. Gold was selected as the conductor material for the preferred embodiment. A layer of glass 46 is deposited over the resistor element 42. One way of forming glass layer 46 is to mix powdered glass with an organic solvent and screen print the mixture on the substrate. The glass layer can also be formed using a doctor blade or brushing the mixture on. The layer of glass 46 is then dried but not fired yet. This provides a firm surface on which to deposit the catalytic support structure 50, but still enables the glass to act as an adhesion promoter when the structure is subsequently fired.

The catalytic support structure 50 comprises high surface area particles such as powdered alumina. The particles can be calcined before applying them to the sensor structure to help assure that they have a high surface area for receiving a catalyst coating. The alumina particles can be combined with aluminum hydroxide or a similar substance to form a paste for application. The paste can be applied with thick film techniques such as screen printing.

After catalytic support structure 50 is applied the entire assembly is fired at the proper firing profile for the glass employed. This will reflow the glass and cause it to firmly adhere to both the alumina particles and substrate 12. It is important that the glass bond very firmly to both the substrate and catalytic support because if the alumina particles flake off, the sensor will no longer function. In principle, any glass film formation, including many commercially available varieties such as GA-4 from Nippon Electric Glass, can be used as described above, provided it has the property of adhering to both substrate 12 and the catalytic support structure 50. A temperature of 700 degrees centigrade for 1 hour is sufficient to reflow the GA-4 glass.

The final step is to apply a catalyst to catalytic support structure 50. In the preferred embodiment for a hydrocarbon sensor, platinum is used for the catalyst. The platinum is applied as a chloroplatinic acid solution using a dropper or other suitable technique. Afterwards the entire structure is again fired at about 500 degrees centigrade for 1 hour to reduce the acid to platinum.

Figure 7:
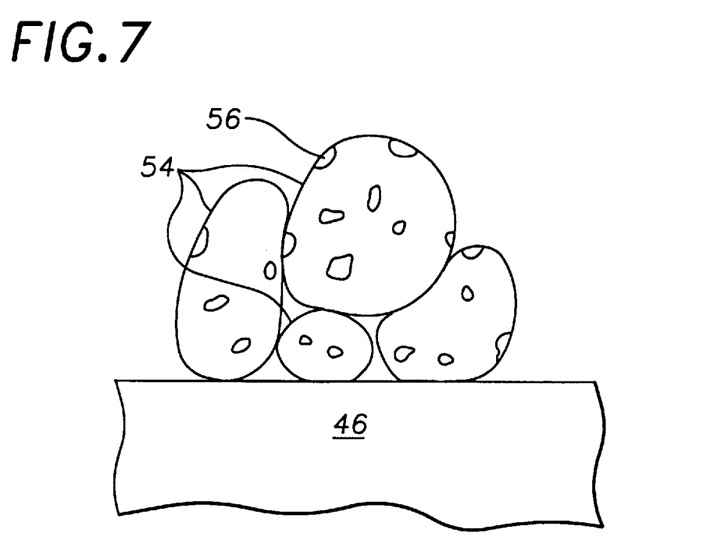
FIG. 7 is an enlargement of a portion of FIG. 6 showing the catalyst support structure.

The final catalytic support structure, as shown by the enlarged view in FIG. 7, comprises alumina particles 54 adhered to glass layer 46. The particles vary in size and shape and the surface may include pores 56. When the chloroplatinic acid is applied and dried as described above, the surfaces of particles 54, including the surfaces of pores 56, will be covered by a very fine layer of platinum.

Figure 8:
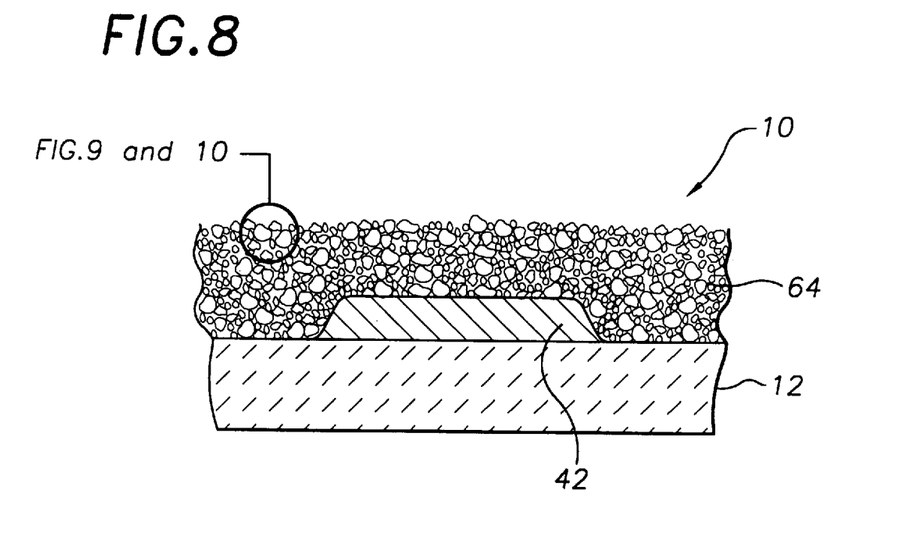
FIG. 8 is a cross-section of FIG. 5 taken through section a-a showing another embodiment for a compounded catalytic structure before firing.

In FIG. 8, a cross section taken through resistor element 42 is depicted. Resistor element 42 can be deposited on substrate 12 using any conventional thick or thin film technique since the deposit is robust enough to withstand the environment of an auto exhaust system and the thermal coefficient of resistivity is high enough so that the resistor will respond to temperature changes from catalytic reactions on the overlaid support structure. The material used to form resistor element 42 can be selected using these same criteria. In the preferred embodiment, it was found that platinum was a satisfactory material for resistor element 42 and that screen printing proved to be a suitable deposition method.

Figure 9:
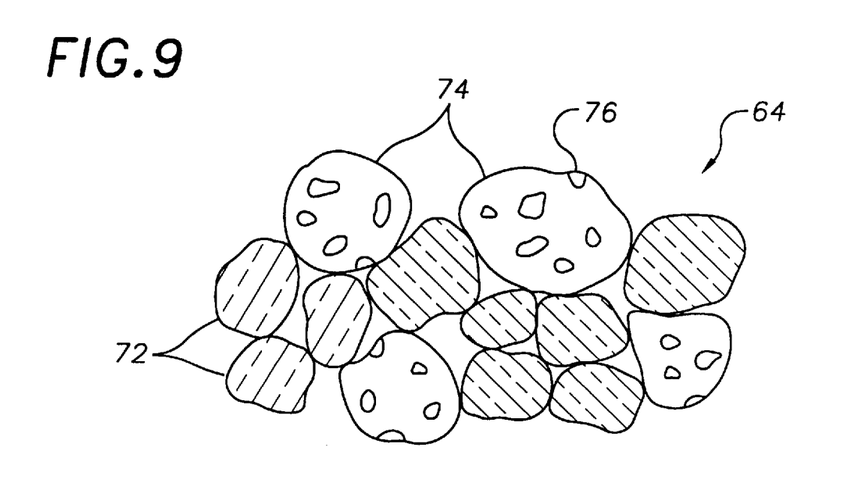
FIG. 9 is an enlargement of the circled portion of FIG. 8 showing greater detail of the catalyst support structure.
Figure 10:
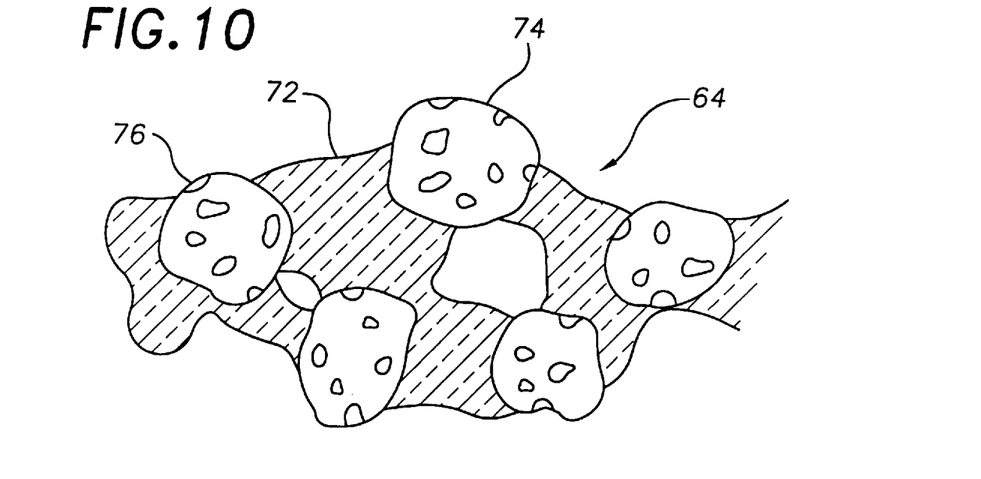
FIG. 10 shows what the structure of FIG. 9 looks like after it has been fired, and the glass has been reflowed.

As shown in FIG. 9 and 10, the catalyst support structure 64, comprises a mixture of alumina particles 74 and powdered glass 72. In the preferred embodiment, the mixture incudes 20% LaRoche V700 alumina and 80% GA-4 glass from Nippon Electric Glass. The alumina is calcined at about 600 degrees Centigrade for 1 hour before it is added to the mixture. This helps assure that the alumina will have a high surface area for a catalyst coating. Sufficient screening agent is added to the mixture to obtain a paste like consistency. The screening agent used in the preferred embodiment is comprised of an organic solvent, a rheology modifying solid and a wetting agent.

The mixture is deposited over the resistor element 42. Screen printing is one suitable method of depositing the mixture; although it can also be deposited using a doctor blade, brushing etc. After catalytic support structure 64 is applied, the entire assembly is heated at a temperature that will reflow the glass employed. A temperature of 700 degrees centigrade for 1 hour is sufficient to reflow the GA-4 glass 72, and cause it to firmly adhere to both the alumina particles 74 and substrate 12 as shown in FIG. 10. It is important that the glass bond very firmly to both the substrate and catalytic support because if the alumina particles flake off, the sensor will no longer function.

The final step is to apply a catalyst to catalytic support structure 64. In the preferred embodiment for a hydrocarbon sensor, platinum is used for the catalyst. The platinum is applied as a chloroplatinic acid solution using a dropper or other suitable technique. Afterwards the entire structure is reheated at a temperature that is high enough to reduce the acid to platinum. A temperature of 500 degrees centigrade was used for the preferred embodiment.

Alumina particles 74 vary in size and shape and the surface may include pores 76. When the chloroplatinic acid is applied and dried as described above, the surfaces of particles 74, including the surfaces of pores 76, will be covered by a very fine layer of platinum. Of course, some platinum will also adhere to the surfaces of glass 72.

Operation of the Sensor

The key to the operation of the sensor is the catalytic reaction of the gas to be sensed and the ability of the resistor element to respond to this reaction by a resulting change in its resistance. For example, as a hydrocarbon gas contacts the platinum catalyst, a chemical reaction occurs in which the hydrocarbon is combusted and heat is generated. The greater the quantity of hydrocarbons, the more heat is produced, thus causing the resistance of resistor element 42 to rise accordingly. The resistance of resistor element 42 is then compared to the resistance of a reference sensor (not shown), which is in the same environment and of the same design, except that it is not covered with a catalyst. The difference in the resistance between resistor element 42 and the reference sensor (not shown) is due to the heat generated by the catalytic reaction. The resistance difference indicates the concentration of hydrocarbons in an exhaust stream.

Variations of the Preferred Embodiment

Although the illustrated embodiments discuss the arrangement of the sensor and signal conditioning circuitry 14 to be on a single base, one skilled in the art will realize that the preferred embodiment would work with most any arrangement. For example, the signal conditioning circuitry 14 could be on a separate base, where the sensor element containing base is, for example, solder connected to the signal conditioning circuit containing base. Additionally, the second base containing the conditioning circuitry could also be a printed circuit board and not ceramic material like the sensor element base.

Eventhough the disclosure discusses the sensing of hydrocarbon, one skilled in the art of gas sensors would understand that this invention is applicable to any combustible gas that is needing to be detected. For example, if hydrogen were to be detected, the heating fixed target temperature for the sensor elements could be around 100 degrees Celsius. An application for a hydrogen sensor would be around a battery enclosure. A set of batteries on an electric car could use a sensor to monitor explosive fumes. Although the preferred embodiment discusses the location of the catalyzed sensor element to be closest to the far end of the sensor, ie. sensor element 21, it is equally workable to have the catalyzed sensor to be located furthest away from the top of the sensor base, ie. sensor elements' 20 location. Thus, a reversal of the positions of the sensor elements is often needed dependent upon the orientation of the overall gas sensor in the gas stream. In these variations, it is still possible to have the heated gas stream portion 29 not contact the reference sensor elements 20 or 21 dependent upon the orientation design.

A further variation of the preferred embodiment is to have the longitudinal axis at most any angle to the gas stream that would allow rotation about the axis that would not have the catalyzed heated gas stream portion contact the reference sensor. However, the present invention works especially well if the whole sensor were inserted into the gas stream at a right angle. However, for example, the sensor housing could be at an acute angle oriented any way in the gas stream. If oriented toward the gas stream, of course the catalyzed sensor would be located below the non-catalyzed sensor (ie. further away from the one end of the base). In this arrangement, the sensor base 12 could be rotated about the longitudinal axis without having the heated gas stream potion 29 contacting the reference sensor elements. If the acutely angled sensor housing were facing downstream, however, the catalyzed sensor element would have to be the top most element with the reference sensor receiving the gas stream 27 first.

While the invention has been taught with specific reference to these embodiments, someone skilled in the art will recognize that changes can be made in form and detail without departing from the spirit and the scope of the invention. The described embodiments are to be considered in all respects only as illustrative and not restrictive. The scope of the invention is, therefore, indicated by the appended claims rather than by the description. All changes that come within the meaning and range of equivalency of the claims are to be embraced within their scope.

What is claimed and desired to be secured by United States Patent is:

1. A gas detector, for detecting concentrations of a gas in a mixture of gases in a gas stream comprising:
    a) a wheatstone bridge circuit, having:
        a1) a first and second bridge,
        a2) a power supply node electrically coupling the first and second bridge at one end,
        a3) a ground node electrically coupling the first and second bridge at another end, and
        a4) a first and second metered node located on the first and second bridge respectively;
    b) a first catalytic sensor element, located on the first bridge between the power node and first metered node;
    c) a second catalytic sensor element, located on the second bridge between the ground node and second metered node;
    d) a first reference sensor element, located on the first bridge and in series with the first catalytic sensor element, and coupled between the first metered node and the ground node;
    e) a second reference sensor element, located on the second bridge and in series with the second catalytic sensor element, and coupled between the second metered node and the power node; and
    f) the first and second reference sensor elements and the first and second catalytic sensor elements designed to be simultaneously exposed to the same gas mixture in the gas stream.

2. The gas detector of claim 1, wherein the gas detector further comprises a base having one end that is positioned in the gas stream, the wheatstone bridge circuit located on the one end thereof.

3. The gas detector of claim 2, wherein during operation of the gas detector, a heated gas steam portion is created as the gas stream passes over the first and second catalyzed sensor element, the first and second catalyzed sensor elements and the first and second sensor elements are positioned on the base so that the heated gas stream portion will not contact the first or second reference sensor element.

4. The gas detector of claim 3, wherein the base includes a catalyzed sensor section for mounting both the first and second catalyzed sensor elements on opposing sides thereof.

5. The gas detector of claim 4, wherein the base includes a sensor section for mounting both the first and second sensor elements on opposing sides thereof.

6. The gas detector of claim 5, wherein the catalyzed sensor section and the sensor section has a void on at least two sides thereof.

7. The gas detector of claim 1, wherein the gas detector further includes signal conditioning circuitry,, electrically coupled to the wheatstone bridge circuit for conditioning signals from the wheatstone bridge circuit.

8. The gas detector of claim 7, wherein the base includes:
a conditioning circuitry section for mounting the conditioning circuitry on the base; and
an extension section on the base for locating the conditioning circuitry section away from the wheatstone bridge circuit.

9. The gas detector of claim 8, wherein the conditioning circuitry section is located on the base at a location in a temperature range under 150 degrees Celsius.

10. A gas detector for detecting a concentration of gas in a mixture of gases in a gas stream, comprising:
a) a wheatstone bridge circuit, having:
a1) a first sensor element and a first catalyzed sensor element coupled in series on a first bridge of the wheatstone bridge circuit;
a2) a second sensor element and a second catalyzed sensor element coupled in series on a second bridge of the wheatstone bridge circuit and in opposite order to the first bridge; and
b) a base having one end that is positioned in the gas stream, the wheatstone bridge circuit located on the one end thereof such that the first and second sensor elements and the first and second catalyzed sensor elements are designed to be simultaneously exposed to the gas stream at the same location.

11. The gas detector of claim 10, wherein during operation of the gas detector, a heated gas stream portion is created as the gas stream passes over the first and second catalyzed sensor elements, the first and second catalyzed sensor element and the first and second sensor elements are positioned on the base so that the heated gas stream portion will not contact the first or second sensor element.

12. The gas detector of claim 11, wherein the base includes a catalyzed sensor section for mounting both the first and second catalyzed sensor elements on opposing sides thereof.

13. The gas detector of claim 12, wherein the base includes a sensor section for mounting both the first and second sensor elements on opposing sides thereof.

14. The gas detector of claim 13, wherein the catalyzed sensor section and the sensor section has a void on at least two sides thereof.

15. The gas detector of claim 10, wherein the gas detector further includes signal conditioning circuitry, electrically coupled to the wheatstone bridge circuit, for conditioning signals from the wheatstone bridge circuit.

16. The gas detector of claim 15, wherein the base includes:
a conditioning circuitry section for mounting the conditioning circuitry on the base; and
an extension section on the base for locating the conditioning circuitry section away from the wheatstone bridge circuit.

17. The gas detector of claim 16, wherein the conditioning circuitry section is located on the base at a location in a temperature range under 150 degrees Celsius.

18. The gas detector of claim 10, further comprising a signal conditioning circuit electrically coupled to receive a first and second voltage from the first and second bridges, respectively.

19. The gas detector of claim 18, wherein in response to detection of a gas the first voltage decreases and the second voltage increases.

20. The gas detector of claim 19, wherein a difference between the first decreased voltage and the second increased voltage has a magnitude greater than the change in magnitude of either the first or second voltage.

21. The gas detector of claim 19, wherein a difference between the first decreased voltage and the second increased voltage has a magnitude twice the magnitude of the change in magnitude of either the first or second voltage.

22. The gas detector of claim 1, further comprising a signal conditioning circuit electrically coupled to receive a first and second voltage from the first and second metered nodes, respectively.

23. The gas detector of claim 22, wherein in response to detection of a gas the first voltage decreases and the second voltage increases.

24. The gas detector of claim 23, wherein a difference between the first decreased voltage and the second increased voltage has a magnitude greater than the change in magnitude of either the first or second voltage.

25. The gas detector of claim 23, wherein a difference between the first decreased voltage and the second increased voltage has a magnitude twice the magnitude of the change in magnitude of either the first or second voltage.

26. The gas detector of claim 1, wherein the gas stream generally has the same chemical composition throughout.

27. The gas detector of claim 10, wherein the gas stream generally has the same chemical composition throughout.

* * * * *